(12) United States Patent
Ensley

(10) Patent No.: US 6,808,707 B2
(45) Date of Patent: Oct. 26, 2004

(54) WOUND HEALING COMPOSITIONS AND METHODS USING TROPOELASTIN AND LYSYL OXIDASE

(75) Inventor: Burt D. Ensley, Newtown, PA (US)

(73) Assignee: Matrix Design, New York, NY (US)

(*) Notice: Subject to any disclaimer, the term of this patent is extended or adjusted under 35 U.S.C. 154(b) by 0 days.

(21) Appl. No.: 09/498,305

(22) Filed: Feb. 4, 2000

(65) Prior Publication Data

US 2002/0150564 A1 Oct. 17, 2002

(51) Int. Cl.⁷ .................. A61K 38/39; A61K 38/44; A66L 17/08; C12N 9/02; C07K 14/78
(52) U.S. Cl. .................. 424/94.4; 424/422; 424/445; 424/484; 435/189; 530/353
(58) Field of Search .................. 424/94.4, 422, 424/445, 484; 435/189, 69.1, 184; 530/353, 350

(56) References Cited

U.S. PATENT DOCUMENTS

| | | | |
|---|---|---|---|
| 4,837,024 A | | 6/1989 | Michaeli .................. 424/446 |
| 5,250,516 A | * | 10/1993 | Urry et al. .................. 514/17 |
| 5,254,132 A | | 10/1993 | Barley et al. .................. 606/214 |
| 5,292,362 A | | 3/1994 | Bass et al. .................. 106/124 |
| 5,352,461 A | | 10/1994 | Feldstein et al. .................. 424/493 |
| 5,521,087 A | * | 5/1996 | Lee et al. .................. 435/366 |
| 5,552,162 A | * | 9/1996 | Lee .................. 424/646 |
| 5,552,452 A | | 9/1996 | Khadem et al. .................. 522/63 |
| 5,614,587 A | | 3/1997 | Rhee et al. .................. 525/54.1 |
| 5,616,689 A | | 4/1997 | Shenoy et al. .................. 530/536 |
| 5,667,839 A | | 9/1997 | Berg .................. 426/657 |
| 5,693,341 A | | 12/1997 | Schroeder et al. .................. 424/488 |
| 5,700,688 A | * | 12/1997 | Lee et al. .................. 435/287.1 |
| 5,726,040 A | | 3/1998 | Ensley et al. .................. 435/69.1 |
| 5,744,545 A | | 4/1998 | Rhee et al. .................. 525/54.1 |
| 5,753,699 A | | 5/1998 | Gregg et al. .................. 514/527 |
| 5,756,350 A | * | 5/1998 | Lee et al. .................. 435/325 |
| 5,773,577 A | * | 6/1998 | Cappello .................. 530/350 |
| RE35,862 E | | 7/1998 | Steiner et al. .................. 425/455 |
| 5,804,594 A | * | 9/1998 | Murad .................. 514/474 |
| 5,891,558 A | * | 4/1999 | Bell et al. .................. 428/218 |
| 5,969,106 A | * | 10/1999 | Rothstein et al. .................. 530/353 |
| 6,153,292 A | * | 11/2000 | Bell et al. .................. 428/305.5 |
| 6,179,872 B1 | * | 1/2001 | Bell et al. .................. 623/11.11 |
| 6,232,458 B1 | * | 5/2001 | Weiss et al. .................. 536/23.2 |
| 6,277,622 B1 | * | 8/2001 | Weiss .................. 435/252.3 |
| 6,358,539 B1 | * | 3/2002 | Murad .................. 424/725 |
| 6,372,228 B1 | * | 4/2002 | Gregory .................. 424/400 |
| 6,489,446 B1 | * | 12/2002 | Rothstein et al. .................. 530/353 |
| 6,667,051 B1 | * | 12/2003 | Gregory .................. 424/443 |
| 6,676,977 B2 | * | 1/2004 | Murad .................. 424/728 |

FOREIGN PATENT DOCUMENTS

WO    WO 98/06830    2/1998

OTHER PUBLICATIONS

Bedell–Hogan, D., et al., 1993, "Oxidation, cross–linking, and insolubilization of recombinant tropoelastin by purified lysyl oxidase", The Journal of Biological Chemistry, vol. 268, No. 14, pp. 10345–10350.*

(List continued on next page.)

Primary Examiner—Ponnathapura Achutamurthy
Assistant Examiner—William W. Moore
(74) Attorney, Agent, or Firm—Brenda Herschback Jarrell; C. Hunter Baker; Choate, Hall & Stewart

(57) ABSTRACT

The present invention provides compositions and methods for promoting wound healing. The composition comprises virgin monomers of tropoelastin and lysyl oxidase. When the lysyl oxidase comes in contact with the tropoelastin, cross-linking of the tropoelastin monomers will occur to form elastin. Contacting the tropoelastin and lysyl oxidase together and applying the mixture to a wound before substantial cross-linking has occurred promotes wound healing by holding the damaged tissue together, increasing the rate of healing, and decreasing the amount of scarring.

10 Claims, 1 Drawing Sheet

OTHER PUBLICATIONS

Bashir et al., "Characterization of the Complete Human Elastin Gene" *J. Biol. Chem.* 264(15):8887–8891, 1989.

Bohen et al., "Hold 'Em and fold 'Em: Chaperones and Signal Transduction" *Science* 268(5215):1303–4, 1995.

Bressan et al., "Repeating Structure of Chick Tropoelastin Revealed by Complementary DNA Cloning" *Biochemistry* 26(6):1497–1503, 1987.

Clark, "Cutaneous Tissue Repair: Basic Biologic Considerations" *Journal of the American Academy of Dermatology* 13(5):701–728, 1985.

Compton et al., "Skin Regenerated from Cultured Epithelial Autografts on Full–Thickness Burn Wounds from 6 Days to 5 Years After Grafting" *Lab. Invest.* 60:600, 1989.

Contente et al., "Epigenetic Inhibition of Lysyl Oxidase Transcription After Transformation By Ras Oncogene" *Mol. Cell. Biochem.* 194:79–91, 1999.

Cronlund et al., "Comparison of Lysyl Oxidase From Bovine Lung and Aorta" *Connective Tissue Research* 15:173–185, 1986.

deVries et al., "Reduced Wound Contraction and Scar Formation in Punch Biopsy Wounds. Native Collagen Derman Substitutes. A Clinical Study." *British Journal of Dermatology* 132:690–697, 1995.

Fink, "Chaperone–Mediated Protein Folding" *Physiol. Rev.* 79(2):425–49, 1999.

Fornieri et al., "Lysol Oxidase Activity and Elastin/Glycosaminoglycan Interactions in Growing Chick and Rat Aortas" *The Journal of Cell Biology* 105:1463–1469, 1987.

Hämäläinen et al., "Molecular Cloning of Human Lysyl Oxidase and Assignment of the Gene to Chromosome 5q23.3–31.2" *Genomics* 11:508–516, 1991.

Hämäläinen et al., "Structure of the Human Lysyl Oxidase Gene" *Genomics* 17(3):544–548, 1993.

Harris et al., "Reaction of Lysyl Oxidase with Soluble Protein Substrates: Effect of Neutral Salts" *Archives of Biochemistry and Biophysics* 190(1):227–223, 1978.

Indik et al., "Alternative Splicing of Human Elastin mRNA Indicated by Sequence Analysis of Cloned Genomic and Complementary DNA" *Proc. Natl. Acad. Sci. USA* 84:5680–5684, 1987.

Kagan, "Characterization and Regulation of Lysyl Oxidase" *Biology of Extracellular Matrix* 1:321, 1986.

Kagan, "Lysyl Oxidase: Mechanism, Regulation and Relationship to Liver Fibrosis"*Path. Res. Pract.* 190:910–919, 1994.

Kagan, et al., "Control of Elastin Metabolism by Elastin Ligands—Reciprocal Effects on Lysyl Oxidase Activity" *Journal of Biological Chemistry* 256(11):5417–5421, 1981.

Kagan, et al., "Purification and Properties of Four Species of Lysyl Oxidase from Bovine Aorta" *Biochem. J.* 177:203–214, 1979.

Kagan, et al., "Repeat Polypeptide Models of Elastin as Substrates For Lysyl Oxidase" *Journal of Biological Chemistry* 225(8):3656–3659, 1980.

Kuivaniemi et al., "Human Placental Lysyl Oxidase" *The Journal of Biological Chemistry* 259(11):6996–7002, 1984.

Lamme et al., "Extracellular Matrix Characterization During Healing of Full–Thickness Wounds Treated With a Collagen/Elastin Dermal Substitute Shows Improved Skin Regeneration in Pigs" *The Journal of Histochemistry and Cytochemistry* 44(11):1311–1322, 1996.

Martin, "Wound Healing—Aiming for Perfect Skin Regeneration" *Science* 276:75–81, 1997.

McDaniel et al., "Treatment of Stretch Marks with the 585–nm Flashlamp–pumped Pulsed Dye Laser" *Dermatol. Surg.* 22:332–337, 1996.

Mecham, "Elastin Synthesis and Fiber Assembly" *Annals New York Academy of Sciences* 624:137–146, 1991.

Merrifield, "New Approaches to the Chemical Synthesis of Peptides" *Recent Prog. Hormone Res.* 23:451–482, 1967.

Parks et al., "Tropoelastin Heterogeneity: Implications for Protein Function and Disease" *American Journal of Respiratory Cell and Molecular Biology* 2:399–406, 1990.

Penoff, J., "Skin Closures Using Cyanoacrylate tissue adhesives. Plastic Surgery Educational Foundation Data Committee. Device and Technique Assessment." *Plas. Reconstr. Surg.* 103(2):730–1, 1999.

Pierce et al., "Heterogeneity of Rat Tropoelastin mRNA Revealed by cDNA Cloning" *Biochemistry* 29:9677–9683, 1990.

Raju et al., "Primary Structures of Bovine Elastin A, B and C Deducted from the Sequences of cDNA Clones" *J. Biol. Chem.* 262:5755–5762, 1987.

Ranson et al., "Chaperonins" *Biochem. J.* 333(2):233–42, 1998.

Robicsek et al., "The Use of Cyanoacrylate Adhesive (Krazy Glue) in Cardiac Surgery"0*J. Card. Surg.* 9(3):353–6, 1994.

Romero–Chapman et al., "Purification, Properties and Influence of Dietary Copper on Accumulation and Functional Activity of Lysyl Oxidase in Rat Skin" *Biochem. J.* 257:657–662, 1991.

Rosenbloom et al., "Extracellular Matrix 4: The Elastic Fiber" *The FASEB Journal* 7:1208–1218, 1993.

Siegel, "Lysyl Oxidase" *Int Rev. Connect. Tissue Res.* 8:73, 1979.

Shackleton et al., "Purification of Lysyl Oxidase From Piglet Skin by Selective Interaction with Sephacryl S–200" *Biochem. J.* 266:917–919, 1990.

Simon et al, "Lacerations Against Langer's Lines: To Glue or Suture?" *J. Emerg. Med.* 16(2):185–9, 1998.

Stassen, "Properties of Highly Purified Lysyl Oxidase From Emryonic Chick Cartilage" *Biochimica et Biophysica Acta* 438:49–60, 1976.

Sullivan et al., "Evidence for Structural Similarities in the Multiple Forms of Aortic and Cartilage Lysyl Oxidase and a Catalytically Quiescent Aortic Protein," *J. Biol. Chem.* 257:13520, 1982.

Tebala et al., "The Use of Cyanoacrylate Tissue Adhesive in High–Risk Intestinal Anastomoses" *Surg. Today* 25(12):1069–72, 1995.

Trackman et al., "Post–translational Glycosylation and Proteolytic Processing of a Lysyl Oxidase Precursor" *The Journal of Biological Chemistry* 267(12):8666–8671, 1992.

Trackman et al., "Cloning of Rat Aorta Lysyl Oxidase cDNA: Complete Codons and Predicted Amino Acid Sequence" *Biochemistry* 29:4863–4870, 1990.

Uitto et al., "Molecular Biology and Pathology of Human Elastin" *Biochemical Society Transactions* 19:824–829, 1991.

Woodley et al., "Cutaneous Wound Healing: A Model For Cell–Matrix Interactions" *J. Am. Acad. Dermatol.* 12:420–433, 1985.

Wu et al., "Characterization and Development Expression of Chick Aortic Lysyl Oxidase" *The Journal of Biological Chemistry* 267(34):24199–24206, 1992.

Yeh et al., "Structure of the Bovine Elastin Gene and S1 Nuclease Analysis of Alternative Splicing of Elastin mRNA in the Bovine Nuchal Ligament"0 *Biochemistry* 28:2365–2370, 1989.

Majesky, et al., "Rat Carotid Neointimal Smooth Muscle Cells Reexpress a Developmentally Regulated mRNA Phenotype During Repair of Arterial Injury", *Circ. Res.* 71(4): 759–768, 1992.

Vrhovski, et al., "Biochemistry of Tropoelastin", *Eur. J. Biochem.* 258: 1–18, 1998.

International Search Report issued for corresponding PCT application PCT/US01/03172.

* cited by examiner

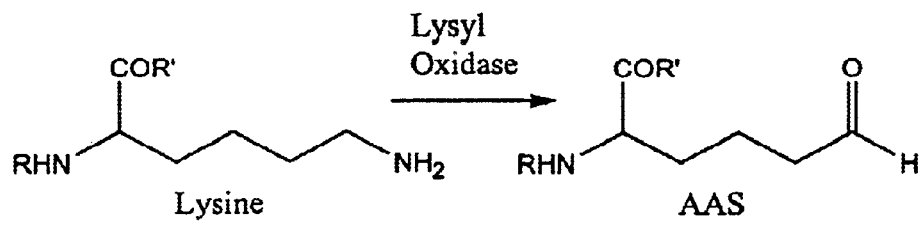
Non-Enzymatic Condensation Cross-Linking Reactions
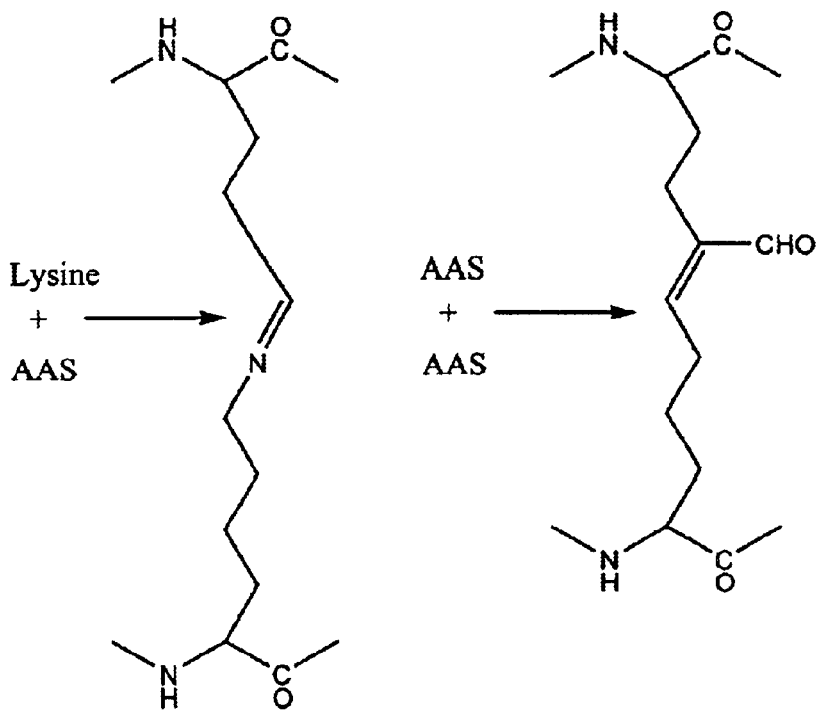
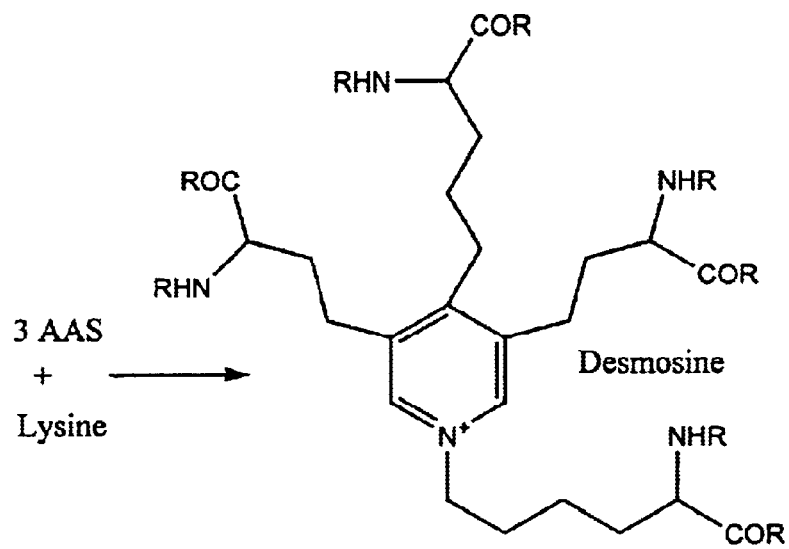

WOUND HEALING COMPOSITIONS AND METHODS USING TROPOELASTIN AND LYSYL OXIDASE

BACKGROUND OF THE INVENTION

Wound healing is a complex biological process that involves many different cell types, many different cytokines, the extracellular matrix (ECM), and numerous interactions among them. Most wounds heal rapidly and efficiently within a week or two; however, the result is neither aesthetically nor functionally perfect. Wound contraction and scar formation are currently unavoidable results of wound healing. Scar tissue is less flexible than normal skin and can be cosmetically disfiguring, and wound contraction can lead to joint disablement (Lamme et al., *J. Histochem. Cytochem.* 44:1311, 1996). Scars lack elastin and consist of poorly reconstituted collagen matrix in dense parallel bundles rather than the mechanically efficient basket-weave meshwork of collagen in unwounded dermis (Martin, *Science* 276:75, 1997). Two major goals of wound-healing biology are more rapid wound healing and more perfect reconstruction of the damaged parts. Compositions and methods useful in accomplishing these goals are currently needed.

Wound Healing

Wound healing has been divided into a number of overlapping phases. These include fibrin clot formation, recruitment of inflammatory cells, reepitheliazation, and matrix formation and remodeling. Immediately after tissue injury, blood vessel disruption leads to the extravasation of blood and concomitant platelet aggregation and blood coagulation resulting in fibrin clot formation. Activated platelets trapped within the fibrin clot degranulate and release a variety of cytokines and growth hormones. These cytokines and growth hormones help to recruit inflammatory cells to the site of injury, to stimulate angiogenesis, and to initiate the tissue movements associated with reepitheliazation and connective tissue contraction.

Neutrophils and monocytes are recruited to the site of injury by a number of chemotactic signals including the growth factors and cytokines released by the degranulating platelets, formyl methionyl peptides cleaved from bacterial proteins, and the by-products of proteolysis of fibrin and other matrix proteins. Neutrophil infiltration ceases after a few days, but macrophages continue to accumulate by continued recruitment of monocytes to the wound site. Activated macrophages release growth factors and cytokines thereby amplifying the earlier signals from the degranulating platelets.

Formation of granulation tissue and reepithelialization of the wound site begins after several hours (Clark, *J. Am. Acad. Dermatol.* 13:701, 1985). Reepithelialization is performed by the basal keratinocytes which lose their attachments to the basal lamina and crawl over the provisional matrix of fibrin and fibronectin, and underlying matrix. Some hours after the onset of migration, epidermal cells begin to reproduce and thereby provide the cells needed to replace those lost during the injury. Keratinocyte proliferation is regulated by keratinocyte growth factor and members of the epidermal growth factor (EGF) family. In order to migrate through the fibrin clot, the keratinocytes must dissolve the fibrin barrier in front of them. Plasmin is the chief fibrinolytic enzyme used in this process. Reepitheliazation is made easier by the underlying contractile connective tissue, which shrinks to bring the wound margins toward one another. Epidermal migration ceases when the wound surface has been covered by a monolayer of cells.

Cells of the new epidermis undergo the standard differentiation program of cells in the outer layers of unwounded epidermis. A new stratified epidermis is, thereby, reestablished from the margins of the wound inward. Matrix formation and remodeling begins simultaneously with reepithelialization. The matrix is constantly altered over the next several months with the elimination of the fibronectin from the matrix and the accumulation of collagen that provides the residual scar with increasing tensile strength. Elastin fibers, which are responsible for the elasticity of tissue, are only detected in human scars years after the injury (Compton et al., *Lab. Invest.* 60:600, 1989).

Methods to Promote Wound Healing

In the past, many methods have been proposed and tested to promote wound healing and limit scarring; however, better methods and compositions are still needed. These older methods include cyanoacrylate tissue adhesives, a combination of epidermal transplantation and a collagen/elastin dermal substitute, application of collagen and glycosaminoglycans to the site of injury, and biocompatible adhesives with collagen.

One of the more popular methods is the use of cyanoacrylate tissue adhesives. These adhesive have been used in place of and in conjunction with sutures. Cyanoacrylate adhesives have been used in cases ranging from cardiac surgery (Robicsek et al., *J. Card. Surg.* 9:353, 1994) to simple lacerations in the pediatric population (Penoff, *Plast. Reconstr. Surg.* 103:730, 1999). One study has found that cyanoacrylate tissue adhesive may be the preferred method in terms of cosmetic appearance for the cutaneous closure of facial lacerations oriented against Langer's lines (Simon et al., *J. Emerg. Med.* 16:185, 1998).

In a study of the healing of full-thickness wounds in pigs, a dermal matrix consisting of native bovine collagen coated with elastin hydrolysate was found to serve as a template for dermal tissue regeneration in combination with an epidermal transplantation. This combination treatment reduced wound contraction and improved tissue regeneration (Lamme et al., *J. Histochem. Cytochem.* 44:1311, 1996).

U.S. Pat. No. 4,837,024, issued Jun. 6, 1989, to Michaeli et al., discloses an article to promote healing of a surface wound. A suspension of particles of collagen and a glycosaminoglycan is contacted with the wound surface. Collagen is a major component of the ECM and helps to promote wound healing. The glycosaminoglycan is chemotactic of fibroblasts and/or endothelial cells. The collagen/glycosaminoglycan is applied to the wound and maintained in contact with the wound for an extended period of time, i.e., during the entire healing process or until at least closure of the wound by new tissue. The application promotes the vascularization of the wound, attracts fibroblasts and endothelial cells, and generally provides a favorable environment for the cells during the healing process.

U.S. Pat. No. 5,614,587, issued Mar. 25, 1997, to Rhee et al., and U.S. Pat. No. 5,744,545, issued Apr. 28, 1998, to Rhee et al., disclose a composition suitable for use as a bioadhesive and a method for using such a composition. The composition comprises fibrillar collagen, a fiber disassembly agent, and a multifunctionally activated synthetic hydrophilic polymer. The collagen and polymer are mixed to initiate cross-linking, the collagen-polymer mixture is then applied to a first surface before substantial cross-linking has occurred, and then a second surface is brought in contact with the first surface. The composition is optically clear so that it could be used in ophthalmic applications, and the composition comprises biocompatible, non-immunogenic components which leave no toxic, potentially inflammatory or immunogenic reaction products at the tissue site of administration.

An invention which would promote healing and lessen scarring would be of great value.

SUMMARY OF THE INVENTION

The present invention provides compositions and methods useful in the promotion of wound healing. These compositions comprise virgin monomers of tropoelastin and the cross-linking enzyme, lysyl oxidase. The method comprises mixing these two components of the composition together and applying them to a wound before substantial cross-linking has occurred. The tropoelastin monomers and lysyl oxidase only come in contact with each other immediately before application to the wound or during application to the wound.

Without wishing to be bound by any particular theory, we propose that the lysyl oxidase catalyzes the oxidative deamination of the lysine residues of the tropoelastin monomers at the site of the wound. Then in a non-enzymatic step, cross-links form between the tropoelastin monomers as well as between tropoelastin monomers and other proteins of the extracellular matrix such as collagen. The cross-linked elastin at the site of injury helps to hold the injured tissue together and thereby promotes healing. The elastin is also chemotactic for fibroblasts, endothelial cells, and inflammatory cells, thereby promoting healing in another manner. Elastin at the site of injury also helps to lessen scarring since scar tissue is devoid of elastin, and elastin is an important component of uninjured skin. The cross-linked elastin also generally provides a favorable environment for the cells that participate in the healing process.

In preferred embodiments of the invention, one or both of the tropoelastin monomers and lysyl oxidase are made recombinantly and purified to homogeneity using standard techniques. The purified tropoelastin and lysyl oxidase may then be suspended in a liquid, such as an aqueous solution (e.g., water or saline) or an organic solvent, or provided in a dry powder form, or in a lyophilized form. These two components, tropoelastin and lysyl oxidase, are kept separate from each other until right before use. In another embodiment, the lysyl oxidase is kept in an inactive from in the presence of the tropoelastin, and the lysyl oxidase not activated until right before use. In yet another embodiment, the two components are applied to the wound separately.

In the method of the present invention, the composition may be applied only once at the time of the injury or more than once over the course of wound healing. The composition of tropoelastin and lysyl oxidase may also be used in conjunction with sutures, staples, or adhesive strips in closing the wound.

The composition of the present invention may also be used in promoting the healing of wounds involving structures with elastic fibers such as arteries, lung tissue, or skin. In particular, the composition may be used in surgeries involving arteries, lungs, or the skin.

In another embodiment of the present invention, the tropoelastin comprises only portions of the tropoelastin protein, preferably containing at least one cross-linking domain. In another embodiment, the lysyl oxidase comprises only an active portion of the enzyme.

The preferred compositions of the present invention are biocompatible, non-toxic, and non-immunogenic, and potentially inflammatory or immunogenic reaction products at the site of administration are avoided.

DESCRIPTION OF THE DRAWINGS

FIG. 1 shows the reaction catalyzed by lysyl oxidase, the oxidative deamination of lysine. A variety of non-enzymatic cross-linking reactions and their products are also shown.

DEFINITIONS

Animal refers to human as well as non-human animals. Non-human animals include mammals, birds, reptiles, amphibians, and fish. Preferably, the non-human animal is a mammal (i.e., a rodent, a mouse, a rat, a rabbit, a monkey, a dog, a cat, or a pig). The term includes transgenic animals.

Biocompatible refers to material that is not toxic to the body, is not carcinogenic, and does not induce inflammation in body tissues.

Biodegradable refers to material that is degraded by normal bodily processes resulting in products which are readily disposable by the body and do not accumulate in the body.

Elastin refers to the cross-linked extracellular matrix protein. In vivo, tropoelastin monomers are cross-linked by lysyl oxidase to form elastin.

Isolated refers to a protein being substantially purified away from contaminating matter. In a preferred embodiment, the protein is greater than 70% pure, greater than 80% pure, or greater than 90% pure. In a particularly preferred embodiment, the protein is greater than 95% pure or 98% pure.

Lysyl oxidase refers to a catalyst which is able to catalyze the oxidative deamination of the amino acid lysine as shown in FIG. 1. In preferred embodiments of the invention, the catalyst is a lysyl oxidase protein enzyme. The genes encoding such enzymes have been cloned from a variety of organisms (Hämäläinen et al., *Genomics* 11:508, 1991; Trackman et al., *Biochemistry* 29:4863, 1990; incorporated herein by reference). In accordance with the present invention, the lysyl oxidase employed is preferably selected to match as closely as possible the individual subject to which the compositions are to be applied. For example, human lysyl oxidase, which has been cloned and characterized (Hämäläinen et al. "Molecular Cloning of Human Lysyl Oxidase and Assignment of the Gene to Chromosome 5q23.3–31.2" *Genomics* 11(3):508–516, 1991; incorporated herein by reference) is preferably utilized in the treatment of wounds involving human tissue. However, in other embodiments the lysyl oxidase may be obtained from any species. When compared to the lysyl oxidase protein of the target species, useful analogs of lysyl oxidase generally exhibit at least 60% homology, preferably at least about 70% homology, more preferably at least about 80% homology, and most preferably at least 90%, 95%, or 99% homology, with a segment of 20 amino acid residues, preferably with more than 40 amino acid residues, more preferably yet with substantially the entire sequence of the target species lysyl oxidase. For compositions to be applied to humans, it is particularly preferred that the lysyl oxidase shows homology to a segment from residues 153–417 and residues 201–417 of the sequence of human lysyl oxidase.

The lysyl oxidase employed in the practice of the present invention may be modified either chemically or genetically in vivo or in vitro. Examples of non-sequence chemical modifications include phosphorylation, acetylation, methylation, carboxylation, hydroxylation, and glycosylation. Examples of genetic modifications include changes in the amino acid sequence, truncation of the polypeptide chain, addition of at least one amino acid, and deletion of at least one amino acid. Techniques for producing such chemical and/or genetic modifications are well known in the art. Any modified protein or polypeptide that retains the ability to catalyze the oxidative deamination of lysine on tropoelastin is useful in the practice of the present invention.

Preferred analogs of lysyl oxidase include human lysyl oxidase or biologically active fragments thereof, whose sequence differ from the wild type by one or more conservative amino acid substitutions or by one or more non-conservative amino acid substitutions, deletions, or insertions which do not abolish lysyl oxidase biological activity. Conservative substitutions typically include the substitution of one amino acid for another with similar characteristics (i.e., substituitions within the following groups: valine, glycine; glycine, alanine; valine, isoleucine, leucine; aspartic acid, glutamic acid; asparagine, glutamine; serine, threonine; lysine, arginine; and phenylalanine, tyrosine). Other conservative substitutions are known by those skilled in the art.

In still other embodiments of the invention, lysyl oxidase may be a non-polypeptide catalyst with the ability to catalyze the oxidative deamination of lysine.

Protein, peptide, orpolypeptide refers to a polymer of amino acids, and these terms are used interchangeably. The polymer may include natural or unnatural amino acids. The protein or polypeptide may be produced in vitro or in vivo via natural, recombinant, synthetic, or other means. The protein or polypeptide may have post-translational modifications or may have been modified chemically to include phosphorylation, glycosylation, famesylation, acetylation, methylation, oxidation of thiols, etc.

Recombinant can refer to organisms, cells, nucleic acids, and proteins. Recombinant cells and organisms are cells and organisms containing recombinant DNA. Recombinant DNA referes to a nucleic acid sequence which is not normally found in nature. Usually this term refers to two or more pieces of DNA spliced together to form an unnatural product. Recombinant protein is protein produced from recombinant DNA (i.e., a nucleic acid which differs from that which occurs in nature). In producing a recombinant protein, the regulatory sequences of the gene encoding the protein are usually different than the ones that occur in the natural gene. The gene may also have been placed in an organism which normally does not possess the gene in order to produce that protein in the desired organism.

Target species refers to the species on which the composition will be applied. A target species can be any animal including humans. Preferably, the target species is mammalian, more preferably a domestic mammal (e.g., dog, cat, cow, horse, rabbit, goat, hamster) or a rodent (e.g., rat, mouse), and most preferably human.

Tropoelastin refers to monomer polypeptides which, when cross-linked, form elastin. The genes encoding tropoelastin have been cloned from a variety of organisms (Bressan et al. "Repeating structure of chick tropoelastin revealed by complementary DNA cloning" *Biochemistry* 26:1497–1503, 1987; Raju et al. "Primary structures of bovine elastin a, b, and c deduced from the sequences of cDNA clones" *J. Biol. Chem.* 262:5755–5762, 1987; Indik et al. "Alternative splicing of human elastin mRNA indicated by sequence analysis of cloned genomic and complementary DNA" *Proc. Natl. Acad. Sci. USA* 84:5680–5684, 1987; Yeh et al. "Structure of the bovine elastin gene and S1 nuclease analysis of alternative splicing of elastin mRNA in the bovine nuchal ligament" *Biochemistry* 28:2365–2370, 1989; Pierce et al. "Heterogeneity of rat tropoelastin mRNA revealed by cDNA cloning" *Biochemistry* 29:9677–9683, 1990; each of which is incorporated herein by reference). In accordance with the present invention, the lysyl oxidase employed is preferably selected to match as closely as possible the individual subject to which the compositions are to be applied. In preferred embodiments of the current invention, the human tropoelastin is utilized in the treatment of a wound involving human tissue. A variety of different isoforms of human tropoelastin are produced in nature (by alternative splicing); any such isoform, or collection of isoforms, may be utilized in the practice of the present invention. In other embodiments, non-human tropoelastin may be employed; however, it is generally desirable to match the species of animal being treated to the species of the tropoelastin being used. The tropoelastin protein may be modified, as compared with naturally occurring human tropoelastin protein, either chemically or genetically in vivo or in vitro. When compared to the tropoelastin protein of the target species, useful analogs of tropoelastin generally exhibit at least 60% homology, preferably at least about 70% homology, more preferably at least about 80% homology, and most preferably at least 90%, 95%, or 99% homolgy, with a segment of 20 amino acid residues, preferably with more than 40 amino acid residues, more preferably yet with substantially the entire sequence of human tropoelastin. Examples of non-sequence chemical modifications include phosphorylation, acetylation, methylation, carboxylation, hydroxylation, and glycosylation. Examples of genetic modifications would be changes in the amino acid sequence, truncation of the polypeptide chain, addition of at least one amino acid, and deletion of at least one amino acid. Techniques for producing such chemical and/or genetic modifications are well known in the art. Tropoelastin can be prepared recombinantly or by chemical synthesis, but it cannot be purified from natural sources because it will have already been crosslinked.

Wild type refers to a nucleic acid sequence or amino acid sequence which is found in nature and has not been mutated. In a preferred embodiment, the wild type sequence is one of the more common sequences for a particular gene or protein found in a particular species. In some instances, there may be several wild type sequences for a protein or gene for one particular species due to multiple alleles of a gene or multiple isoforms of a protein.

Wound refers to damaged biological tissue in the most general sense. In a preferred embodiment, the wound is a laceration of the skin. In other embodiments, the wound may be an abrasion of the skin without two separated parts of tissue which need to be brought together. In still other embodiments, the wound may refer to a surgical incision. In other preferred embodiments, the wound may involve damage to lung tissue, arterial walls, or other organs with elastic fibers.

DETAILED DESCRIPTION OF PREFERRED EMBODIMENTS

As described above, the present invention provides compositions and methods for promoting wound healing. These compositions comprise tropoelastin and lysyl oxidase. The method of the present invention involves contacting these two components together and applying the mixture to a wound before substantial cross-linking of the tropoelastin has taken place. In another embodiment, the tropoelastin and lysyl oxidase are applied separately to the wound. A key aspect of the invention is that the tropoelastin must be applied to the wound before substantial cross-linking of the tropoelastin has occurred. To those skilled in the art, a variety of ways of applying the two substances wherein the tropoelastin is not substantially cross-linked will be clear. With the cross-linking reaction taking place at the wound site, cross-links will form that will hold the tissue together. Also, the new formation of elastin will attract fibroblasts, inflammatory cells, and endothelial cell by chemotaxis, will result in less scarring, and will provide a suitable environment for the cells involved in the healing process.

Elastin

Elastic fibers in the extracellular space of the lungs, dermis, and large blood vessels contribute to the elasticity and resilience of these tissues. These elastic fibers may comprise only a small (2–4%) portion of the dry weight of skin but may comprise greater than 50% of the dry weight of large arteries (Rosenbloom et al., *FASEB J.* 7:1208, 1993). These fibers are composed of amorphous elastin and microfibrils. Microfibrils are a complex of glycoproteins organized as small, 10- to 12-nm-diameter fibrils and serve as the scaffold onto which elastin is assembled. Elastin is the major component (>90%) of the mature elastic fibers and has been well characterized. The elastin protein is initially synthesized as tropoelastin monomers, soluble polypeptides of ca. 72 kDa (Parks et al., *Am. J. Respir. Cell Mol. Biol.* 2:399, 1990).

The tropoelastin gene exists as a single copy in the genome. The gene has been isolated from several species, including human, bovine, chick, and rat (Bressan et al. "Repeating structure of chick tropoelastin revealed by complementary DNA cloning" *Biochemistry* 26:1497–1503, 1987; Raju et al. "Primary structures of bovine elastin a, b, and c deduced from the sequences of cDNA clones" *J. Biol. Chem.* 262:5755–5762, 1987; Indik et al. "Alternative splicing of human elastin mRNA indicated by sequence analysis of cloned genomic and complementary DNA" *Proc. Natl. Acad. Sci. USA* 84:5680–5684, 1987; Yeh et al. "Structure of the bovine elastin gene and S1 nuclease analysis of alternative splicing of elastin mRNA in the bovine nuchal ligament" *Biochemistry* 28:2365–2370, 1989; Pierce et al. "Heterogeneity of rat tropoelastin mRNA revealed by cDNA cloning" *Biochemistry* 29:9677–9683, 1990; each of which is incorporated herein by reference); the entire bovine and human elastin genes have been isolated and sequenced (Indik et al., *Proc. Natl. Acad. Sci. USA* 84:5680, 1987; Yeh et al., Biochemistry 28:2365, 1989; Bashir et al., *J. Biol. Chem.* 264:8887, 1989; each of which is incorporated herein by reference). Elucidation of the amino acid sequence indicates alternating segments of cross-link domains and hydrophobic domains. The cross-link domains are characterized by the presence of lysine residues separated by two to three alanine residues, and the hydrophobic domains are found to be rich in hydrophobic residues such as glycine, alanine, valine, and proline. This composition results in hydrophobic interactions which are thought to be responsible for the elasticity of the fibers. The cross-link and hydrophobic domains are encoded by separate exons of the gene.

Extensive alternative splicing of the primary tropoelastin transcript yields the diversity of tropoelastin isoforms seen at the protein level. The human tropoelastin gene consists of 34 separate exons spanning a total of ca. 45 kB of genomic DNA. Six of these exons have been reported to be subject to alternative splicing (Uitto et al., *Biochem. Soc. Transact.* 19:824, 1991).

Newly synthesized pre-tropoelastin (containing the signal peptide) undergoes intracellular post-translational modifications including hydroxylation of certain proline residues to form 4-hydroxyproline and removal of the signal peptide. The tropoelastin monomers are then secreted into the extracellular milieu where they assemble into functional fibers (fibrillogenesis) and are cross-linked to form insoluble elastin (Uitto et al., *Biochem. Soc. Transact.* 19:824–829, 1991).

The assembly of elastic fibers (fibrillogenesis) takes place at unique sites close to the cell membrane, generally in infoldings of the cell surface. Microfibrils are the first component to appear and are found to be grouped in small bundles near the plasma membrane. Elastin then appears as amorphous material in discrete loci within each microfibrillar bundle. The microfibrils are thought to align the tropoelastin molecules so that the cross-linking regions are juxtaposed. Lysyl oxidase then oxidizes the terminal amino groups on the side chains of the lysine residues of the cross-linking regions. The oxidized side chains then undergo non-enzymatic condensation reactions to form the cross-links. The notion that tropoelastin monomers are secreted from the cell and diffuse onto the surface of growing fibers seems to be inadequate to explain the efficiency of the whole process and the variable forms of elastic fibers in different tissues. Rather, increasing evidence has supported the idea that helper proteins are needed in the secretion and fiber assembly steps. Given that tropoelastin monomers produced in organisms are rapidly incorporated into insoluble elastin fibers, purification of tropoelastin from anything other than recombinant sources is not practical. Thus, in accordance with the present invention, virgin tropoelastin monomers may be provided by any available method, including, for example, chemical synthesis and standard recombinant techniques known in the art.

In one preferred embodiment, the tropoelastin monomers are synthesized using available chemical synthetic methods. For example, tropoelastin monomers can be synthesized using an appropriate solid state synthetic procedure (Steward et al., *Solid Phase Synthesis*, Freemantle, San Francisco, Calif., 1968). A preferred method is the Merrifield process (Merrifield, *Recent Prog. Hormone Res.* 23:451, 1967).

Alternatively, tropoelastin monomers may be prepared by recombinant techniques. Techniques for the overexpression and purification of recombinant proteins in a wide variety of cell types are well known in the art ("Gene Expression Technology," *Methods in Enzymology*, vol. 185 (D. V. Goeddel, ed.), Academic Press Inc., 1990; incorporated herein by reference). Any such techniques can be employed in accordance with the present invention. Since tropoelastin monomers are normally secreted from the cell, a preferred way to produce the monomers for the present invention would be to introduce the gene with the signal sequence intact and under the control of a strong promoter into a cell and grow the recombinant cells in culture. Preferably, the recombinant cells are eukaryotic (i.e., *Saccharomyces cerevisiae*, *Pichia pastoris*), more preferably the cells are of mammalian origin (i.e., COS cell line, CHO cell line), and most preferably the cells are of a human origin. In certain preferred embodiments of the invention, the recombinant cells are derived from human fibroblasts. In another preferred embodiment, the recombinant cells are recombinant bacteria (e.g., *E. coli*). The desired tropoelastin monomers would be secreted into the media, and the protein could be purified to homogeneity from the media. To improve the ease at which the protein could be purified, the cells expressing the tropoelastin would be grown in serum-free media, thereby minimizing the amount of protein in the media to start with. Production of the tropoelastin monomers in mammalian cells such as fibroblasts would insure correct folding and post-translational modification of the protein. This could be important since some of the proline residues in tropoelastin are hydroxylated posttranslationally.

Once the recombinant tropoelastin of the present invention is expressed, the protein may be isolated and purified by standard methods including chromatography (e.g., ion exchange, affinity, size exclusion, and hydroxyapatite chromatography), centrifugation, or differential solubility, or by any other available technique for the purification of proteins (Scopes, *Protein Purification Principles and Prac-* tice *2nd Edition*, Springer-Verlag, New York, 1987; incorporated herein by reference). For immunoaffinity chromatography in particular, the protein may be isolated by binding it to an affinity column comprising antibodies that were raised against that protein and were affixed to a stationary support. Alternatively, affinity tags such as an influenza coat sequence, poly-histidine, or glutathione-S-transferase can be attached to the protein by standard recombinant techniques to allow for easy purification by passage over the appropriate affinity column.

Any method of producing tropoelastin known in the art can be used as long as the tropoelastin is able to be cross-linked to form elastin and does not initiate negative (e.g., immune reactions) reactions once introduced into or applied onto the recipient's body.

If particular isoforms of tropoelastin are needed, the appropriate cDNA(s) can be introduced into the cells for overexpression. Different isoforms of tropoelastin are found in different individuals within a species, in different locations within one individual, and in different tissues within an individual. In preferred embodiments of the present invention, a certain isoform of tropoelastin or mixture of isoforms is used for a particular individual being treated, a particular type of wound, or a particular type of tissue. For example, it may be desirable to provide a composition comprising multiple different tropoelastin isoforms, whose identity and/or relative quantity are selected to match as closely as possible the profile of isoforms naturally produced by the individual to whom the composition is being applied, at the site of application. If the natural isoform distribution in that individual (or a representative thereof, e.g., another member, or an averaged collection of members, of the same species) and/or at that site, is not known in advance it may readily be determined by one of ordinary skill in the art using standard techniques such as, for example, gene sequencing, restriction fragment length polymorphisms, Western blotting, immunoassay, Northern blotting, Southern Blotting, isoelectric focusing, SDS-polyacrylamide gel electrophoresis, etc. In a preferred embodiment, the individual isoforms of tropoelastin might be prepared separately and mixed at specific ratios later to simulate the ratio of isoforms in a specific tissue of an individual. The use of tropoelastin isoforms native to the tissue would minimize any immune reactions.

In another preferred embodiment of the invention, a modified version of tropoelastin is provided which is not susceptible to cross-linking. The tropoelastin may not be susceptible to cross-linking for a number of reasons including, for example, its binding another protein or peptide, or its not being folded correctly. In order for the tropoelastin to be cross-linked, the binding protein or peptide would need to be removed, or the tropoelastin would need to be refolded. The binding peptide or protein may be removed by competing off the peptide or protein; cleavage of the binding peptide or protein; conformational change of one of the proteins; etc. If the tropoelastin is not folded correctly, a protein from the family of chaperonins (e.g., GroEL, GroES) or heat shock proteins (e.g., Hsp60, Hsp40, Hsp70) may be added to re-fold the tropoelastin so that it may be cross-linked. In this embodiment, the virgin tropoelastin monomers and modified lysyl oxidase can be stored together without the risk of cross-linking the tropoelastin monomers.

Lysyl Oxidase

The high degree of cross-linking found in the elastic fibers contributes to their proper function. Lysyl oxidase is the enzyme that catalyzes the oxidative deamination of lysine residues leading to the non-enzymatic condensation of the modified lysine side chains. This same enzyme is involved in collagen cross-link formation as well. All but about 5 of the 34 lysine residues of tropoelastin participate in some form of cross-link resulting in a highly insoluble polymer (Rosenbloom et al., *FASEB J.* 7:1208, 1993).

Lysyl oxidase is an extracellular, copper-requiring enzyme which has been purified to homogeneity from several animal sources and found to have a molecular weight of ca. 30 kDa (Stassen, *Biochim. Biophys. Acta* 438:49, 1976; Siegel, *Int. Rev. Connect. Tissue Res.* 8:73, 1979; Sullivan et al., *J. Biol. Chem.* 257:13520, 1982; Kagan, *Biology of Extracellular Matrix* 1:321, 1986; Kuivaniemi et al., *J. Biol. Chem.* 259:6996, 1984). The genes encoding lysyl oxidase have been cloned from human and rat cDNA libraries (Hämäläinen et al., *Genomics* 11:508 (1991); Trackman et al., *Biochemistry* 29:4863 (1990)).

Oxidation of lysine residues in tropoelastin leads to the formation of $\alpha$-aminoadipic-$\delta$-semialdehyde (AAS). Reaction of a lysine residue with AAS leads to the formation of a dehydrolysinonorleucine cross-link. Reaction of two AAS residues leads to an Aldol condensation product. Tetrafunctional cross-linkages can be formed in elastin from three peptidyl aldehydes (AAS) and one unmodified lysine residue (FIG. 1) (Kagan, *Path. Res. Pract.* 190:910, 1994; incorporated herein by reference).

For the purposes of the present invention, lysyl oxidase can be produced by any available method, including, for example, chemical synthesis, recombinant methods, and purification from a natural source. In a preferred embodiment, lysyl oxidase is produced recombinantly in much the same manner as the tropoelastin (discussed supra). Again, lysyl oxidase is normally secreted so a preferred method of producing and purifying the enzyme would be to secrete it into the media and then purify the protein from the media. If a modified version (i.e., change in amino acid sequence) was needed, the appropriate cDNA could be introduced into the cell to produce the desired mutant protein. Standard techniques for these procedures are known in the art.

In a preferred embodiment of the invention, a modified version of the lysyl oxidase is produced which is inactive initially and can subsequently be converted into an active form. This particular embodiment of the invention allows the tropoelastin and inactive lysyl oxidase to be stored together. Then, prior to application to a wound, the inactive lysyl oxidase is converted to the active form by cleavage of the protein or by a change in pH, temperature, salt concentration, metal ion concentration, etc. The conversion from the inactive form to the active form might even take place at the site of the wound and be caused by a protease or change in pH at the wound site per se.

In another preferred embodiment of the invention, a modified version of lysyl oxidase would be provided which binds to another protein or peptide (binding peptide or protein). The binding of this binding protein or peptide to the modified lysyl oxidase would lead to inactivation of the lysyl oxidase enzyme. In order for the lysyl oxidase to regain its enzymatic activity, the binding protein or peptide would need to be removed. Examples of this approach include competing off the modified lysyl oxidase using another peptide or protein, a small organic molecule, a metal, nucleic acid, polysaccharide, etc.; cleavage of the binding peptide or protein; conformational change of modified lysyl oxidase; and conformational change of the binding protein or peptide.

In a particulary preferred embodiment, a protein from the family of chaperonins (e.g., GroEL, GroES) or heat shock proteins (e.g., Hsp60, Hsp40, Hsp70) may be used as the binding protein, and the lysyl oxidase may be modified by techniques well known in the art to include a binding domain specific for a chaperonin or heat shock protein (Ranson et al, "Chaperonins" *Biochem. J.* 333 (Pt. 2):233–242, Jul. 15, 1998; Fink et al., "Chaperone-mediated protein folding" *Physiol. Rev.* 79(2):425–449, April 1999; each of which is incorporated herein by reference). In this way, the virgin tropoelastin monomers and modified lysyl oxidase bound to a chaperonin or heat shock protein can be stored together without the risk of cross-linking the tropoelastin monomers. After the tropoelastin and lysyl oxidase are applied to a wound or immediately before they are applied to a wound, an agent such as a small molecule (e.g., estrogen) is added to restore lysyl oxidase activity and begin the cross-linking of tropoelastin (Bohen et al., "Hold 'em and fold 'em: chaperones and signal transduction" Science 268(5125): 1303–1304, Jun. 2, 1995; incorporated herein by reference).

Packaging

In one preferred embodiment of the invention, the tropoelastin monomers are be provided in one vial, and the lysyl oxidase are provided in another vial. These proteins might be provided in a dry powder form, in solid form (i.e., lyophilized), in solution, or in suspension. To the proteins may have been added emulsifiers, salts, preservatives, other proteins, nucleic acids, protease inhibitors, antibiotics, perfumes, polysaccharides, adhesive agents, polymers, microfibrils, oils, etc.

In another preferred embodiment, the tropoelastin or the lysyl oxidase, or both, is encapsulated in a biodegradable polymer so that when the composition is applied to a wound, the polymer degrades and the tropoelastin and/or lysyl oxidase is released; the released tropoelastin can then be crosslinked.

Biodegradable polymers are usually based on functional groups such as esters, anhydrides, orthoesters, and amides. Rapidly biodegradable polymers include poly[lactide-co-glycolide], polyanhydrides, and polyorthoesters. Preferred bioerodible polymers include polylactides, polyglycolides, and copolymers thereof, poly(ethylene terephthalate), poly(butyric acid), poly(valeric acid), poly(lactide-co-caprolactone), poly(lactide-co-glycolide), polyanhydrides, polyphosphazenes, poly($\epsilon$-caprolactone), poly(dioxanone), poly(hydroxybutyrate), poly(hydroxyvalerate), polyorthoesters, blends, and copolymers thereof. Examples of biodegradable and biocompatible polymers of acrylic and methacrylic acids or esters include poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), etc. Other polymers which can be used in the present invention include polyalkylenes such as polyethylene and polypropylene; polyarylalkylenes such as polystyrene; poly(alkylene glycols) such as poly(ethylene glycol); poly(alkylene oxides) such as poly(ethylene oxide); and poly(alkylene terephthalates) such as poly(ethylene terephthalate). Additionally, polyvinyl polymers can be used which include polyvinyl alcohols, polyvinyl ethers, polyvinyl esters, and polyvinyl halides. Exemplary polyvinyl polymers include poly(vinyl acetate), polyvinyl phenol, and polyvinylpyrrolidone. Mixtures of two or more of the above polymers could also be used in the present invention.

Some polymeric materials are known to release entrapped compounds upon exposure to a stimulus such as a change in pH or temperature. An examples of microparticles that release as a function of a change in pH include the diketopiperazine particles describes in U.S. Pat. No. 5,352,461 issued on Oct. 4, 1994, to Steiner et al., and the proteinoid formulations described in U.S. Patent Reissue no. 35,862, issued on Jul. 28, 1998.

Application

Methods for using the composition include, for example, mixing the two separate components together immediately before application to the wound (i.e., before substantial cross-linking has occurred). Other preferred embodiments include applying either the tropoelastin or lysyl oxidase and then the other one to the wound site. One particularly preferred embodiment involves application of a composition comprising lysyl oxidase and tropoelastin to a wound and then use of sutures, staples, adhesive strips, or tissue adhesive to hold the tissue together during the healing process.

Another particularly preferred embodiment involves application of the composition more than once during the healing process. Preferred regiments for applying the lysyl oxidase and tropoelastin include several times a day, once a day, once a week, twice a week, once a month, and twice a month. In following each of these regiments, the agents would be mixed immediately before application, or they would be applied separately to the wound.

The lysyl oxidase and tropoelastin are delivered to the wound site using any means to apply a liquid, paste, gel, or solid (e.g., powder). These means include, for example, a brush, a syringe, a spatula, and a container specifically designed to delivery the agents such as a tube with a narrow tip.

In another preferred embodiment of the invention, the composition is applied to a wound resulting from deep trauma or surgery involving the lungs, large arteries, or other tissues with significant amounts of elastic fibers.

Other Embodiments

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:

1. A method for promoting healing of a skin wound comprising steps of:
   providing isolated tropoelastin wherein the tropoelastin has not previously been crosslinked and is therefore available for crosslinking, and isolated lysyl oxidase, which components are kept separated from each other; and
   applying both said tropoelastin and said lysyl oxidase to a skin wound simultaneously or sequentially, so that said tropoelastin is not crosslinked to itself prior to application to the wound.

2. The method of claim 1 wherein tropoelastin is wild type tropoelastin matched to species of recipient.

3. The method of claim 1 wherein tropoelastin comprises a heterogeneous mixture of tropoelastin isoforms.

4. The method of claim 1 wherein the method comprises the additional step of: repeatedly applying the tropoelastin and lysyl oxidase to the wound during the healing process.

5. The method of claim 1 wherein the method comprises the additional step of: approximating separated tissue of the wound using sutures, staples, adhesive strips, or tissue glue.

6. The method of claim 1 wherein the step of applying comprises applying the tropoelastin and lysyl oxidase with a sterile syringe.

7. The method of claim 1 wherein the tropoelastin or lysyl oxidase has been mixed with other materials selected from the group consisting of polymers, emulsifiers, oils, polysaccharides, microfibrils, antimicrobial agents, adhesive agents, and protease inhibitors.

8. A kit comprising tropoelastin wherein the tropoelastin has not previously been crosslinked and is therefore available for crosslinking, and lysyl oxidase in separate compartments.

9. The kit of claim 8 wherein the tropoelastin is wild type tropoelastin.

10. The kit of claim 8 wherein the lysyl oxidase is wild type lysyl oxidase.

* * * * *